United States Patent
Prihoda et al.

(10) Patent No.: US 11,925,572 B2
(45) Date of Patent: Mar. 12, 2024

(54) LOWER LEG ORTHOTIC BRACE

(71) Applicant: DOXA Medical, LLC, Washington, IA (US)

(72) Inventors: Matthew John Prihoda, Washington, IA (US); John Ray Mitchell, Danville, IA (US); Andy Michael Smith, Danville, IA (US); Marcus William Powell, New London, IA (US); Shawn Edward Twyman, Mt. Pleasant, IA (US)

(73) Assignee: DOXA MEDICAL, LLC, Washington, IA (US)

( * ) Notice: Subject to any disclaimer, the term of this patent is extended or adjusted under 35 U.S.C. 154(b) by 183 days.

(21) Appl. No.: 17/144,768

(22) Filed: Jan. 8, 2021

(65) Prior Publication Data
US 2021/0205114 A1  Jul. 8, 2021

Related U.S. Application Data

(60) Provisional application No. 62/958,372, filed on Jan. 8, 2020.

(51) Int. Cl.
*A61F 5/058* (2006.01)
*A61F 5/01* (2006.01)

(52) U.S. Cl.
CPC .......... *A61F 5/0585* (2013.01); *A61F 5/0111* (2013.01)

(58) Field of Classification Search
CPC ...... A61F 5/0585; A61F 5/0111; A61F 5/042; A61F 5/05; A61F 5/0127; A61F 5/3761; A61F 5/0102; A43B 7/18
See application file for complete search history.

(56) References Cited

U.S. PATENT DOCUMENTS

| | | | |
|---|---|---|---|
| 2002/0139009 A1* | 10/2002 | Mark | A43B 7/18 36/100 |
| 2008/0039758 A1* | 2/2008 | Jensen | A61F 5/0111 602/27 |
| 2009/0287128 A1* | 11/2009 | Ingimundarson | A61F 5/0102 602/27 |
| 2010/0137770 A1* | 6/2010 | Ingimundarson | A61F 5/0111 602/27 |
| 2011/0144554 A1* | 6/2011 | Weaver, II | A61F 5/0127 602/27 |
| 2011/0197362 A1* | 8/2011 | Chella | A61F 5/3761 5/650 |
| 2017/0056230 A1* | 3/2017 | Miller | A61F 5/0127 |
| 2019/0269558 A1* | 9/2019 | Sheehan | A61F 5/05 |
| 2020/0206059 A1* | 7/2020 | DeHeer | A61F 5/042 |

* cited by examiner

*Primary Examiner* — Ophelia A Hawthorne
*Assistant Examiner* — Gina McCarthy
(74) *Attorney, Agent, or Firm* — NYEMASTER GOODE P.C.

(57) ABSTRACT

A foot orthotic having a foot support where the foot support includes a thermoplastic outer shell, a closed cell foam liner within the outer shell, and a tongue to secure the user's foot within the foot support. The orthotic also typically has includes a lower leg support that includes a thermoplastic outer shell, a closed cell foam liner within the outer shell, and a strap to secure the orthotic to the user's leg within the lower leg support. A cinching mechanism that typically has a rotatable tightening knob is on the lower leg support, and a tightening cable coupled to the rotatable tightening knob and operably connected to the foot support.

20 Claims, 10 Drawing Sheets

LOWER LEG ORTHOTIC BRACE

CROSS-REFERENCE TO RELATED APPLICATION

This application claims priority to and benefit of U.S. Provisional Patent Application No. 62/958,372, filed on Jan. 8, 2020, entitled "LOWER LEG ORTHOTIC BRACE," the disclosure of which is hereby incorporated herein by reference in its entirety.

BACKGROUND

For certain soft tissue ailments in person's (sometimes a patient) lower legs such as plantar fasciitis or Achilles tendon repair or treatment, it is important for a patient to continue static stretching of soft tissue connective tissues including Achilles tendon and plantar fascia, preserve resting arch position, balance the positioning of intrinsic foot musculature at 90 degrees, provide passive stretching to posterior large muscle flexors, and completely offload anterior compartment extensors and soft tissue kinetics.

SUMMARY

One aspect of the present disclosure includes a custom foot orthotic having a foot support custom fit to a foot, the foot support includes a thermoplastic outer shell, a closed cell foam liner within the outer shell, and a tongue to secure the user's foot within the foot support. The foot support, which includes but is not limited to, a posterior splint, typically prevents lateral movement of the foot when the wearer's foot is engaged with the foot support. When the foot is engaged with the foot support the top of the wearer's foot typically remains largely exposed to the open environment with the exception of the top of the wearer's foot that may be covered by the tongue. The orthotic includes a lower leg support custom fit a lower leg and hinged to the foot support, and including a thermoplastic outer shell, a closed cell foam liner within the outer shell, and a strap to secure the user's leg within the lower leg support. A cinching mechanism having a rotatable tightening knob is on the lower leg support, and a tightening cable coupled to the rotatable tightening knob and operably connected to the foot support. A plurality of channels are in the lower leg and foot support, and the cable is routed through the plurality of channels within the lower leg support and the foot support. The foot support and lower leg support in any aspect of the present disclosure may be unitary or separate structures that may be hingedly connected with one another to form an orthotic structure of the present disclosure.

Another aspect of the present disclosure includes a brace for a person's lower leg and foot that includes a foot support having a thermoplastic outer shell with a channel, a closed cell foam liner within the outer shell, and a tongue securely fastened to the outer shell on a first end; a lower leg support hingedly connected to the foot support, the lower leg support having a thermoplastic outer shell with a channel, a closed cell foam liner within the outer shell, and a strap securely fastened to the outer shell on a first end and a self-fastening device on a second end; a rotatable tightening knob disposed on the lower leg support; and a tightening cable coupled to the rotatable tightening knob, the tightening cable routed within the foot support channel and the lower leg channel, and operably attached to a second end of the tongue.

Another aspect of the present disclosure includes a method for treating a lower extremity ailment of a patient having the steps of creating a lower leg support by forming a lower leg outer shell, fitting a closed-cell foam lower leg inner liner to the inside of the lower leg outer shell, and attaching a securing strap to the lower leg outer shell; creating a foot support by forming a foot outer shell, fitting a closed-cell foam foot inner liner to the inside of the lower leg outer shell, and attaching a securing tongue to the foot outer shell; hingedly attaching the lower leg support to the foot support, attaching a cinching mechanism knob to the lower leg support, attaching a cinching cable to the cinching mechanism knob, routing the cinching cable through channels on the lower leg outer shell and the foot outer shell, and attaching a distal end of the cinching cable to the securing tongue.

Yet another aspect of the present disclosure is generally directed to a method of producing a brace for a person's lower leg and foot. The method typically includes the steps of: forming a lower leg support by creating a lower leg outer shell out of a thermoplastic material, securely attaching a lower leg inner liner to an interior portion of the lower leg outer shell, and securely attaching a first end of a tightening strap to an upper portion of the lower leg outer shell; forming a foot support by creating a foot outer shell out of a thermoplastic material, securely attaching a foot inner liner to an interior portion of the foot outer shell, and securely attaching a first end of a tongue to a first side of the foot outer shell; hingedly attaching the foot support to the lower leg support; rotatably attaching a tightening knob to an upper portion of the lower leg support; operably connecting a tightening cable to the tightening knob; routing the tightening cable through a channel in the lower leg support; routing the tightening cable through a channel in the foot support; and attaching the tightening cable to a second end of the tongue.

Another aspect of the present disclosure is generally directed toward a brace for a person's lower leg and foot that includes a foot support fit to a user's foot where the foot support has a thermoplastic outer shell; a closed cell foam liner within the outer shell; and a tongue to secure the user's foot within the foot support; a lower leg support connected to the foot support, the lower leg support having a thermoplastic outer shell; a closed cell foam liner within the outer shell; a strap to secure the user's leg within the lower leg support; a cinching mechanism having a rotatable tightening knob disposed on the lower leg support and a tightening cable coupled to the rotatable tightening knob and operably connected to the foot support; and a plurality of channels within the lower leg support and the foot support. The tightening cable is typically routed through the plurality of channels within the lower leg support and the foot support.

These and other aspects, objects, and features of the present disclosure will be understood and appreciated by those skilled in the art upon studying the following specification, claims, and appended drawings.

DETAILED DESCRIPTION

Figure 2:
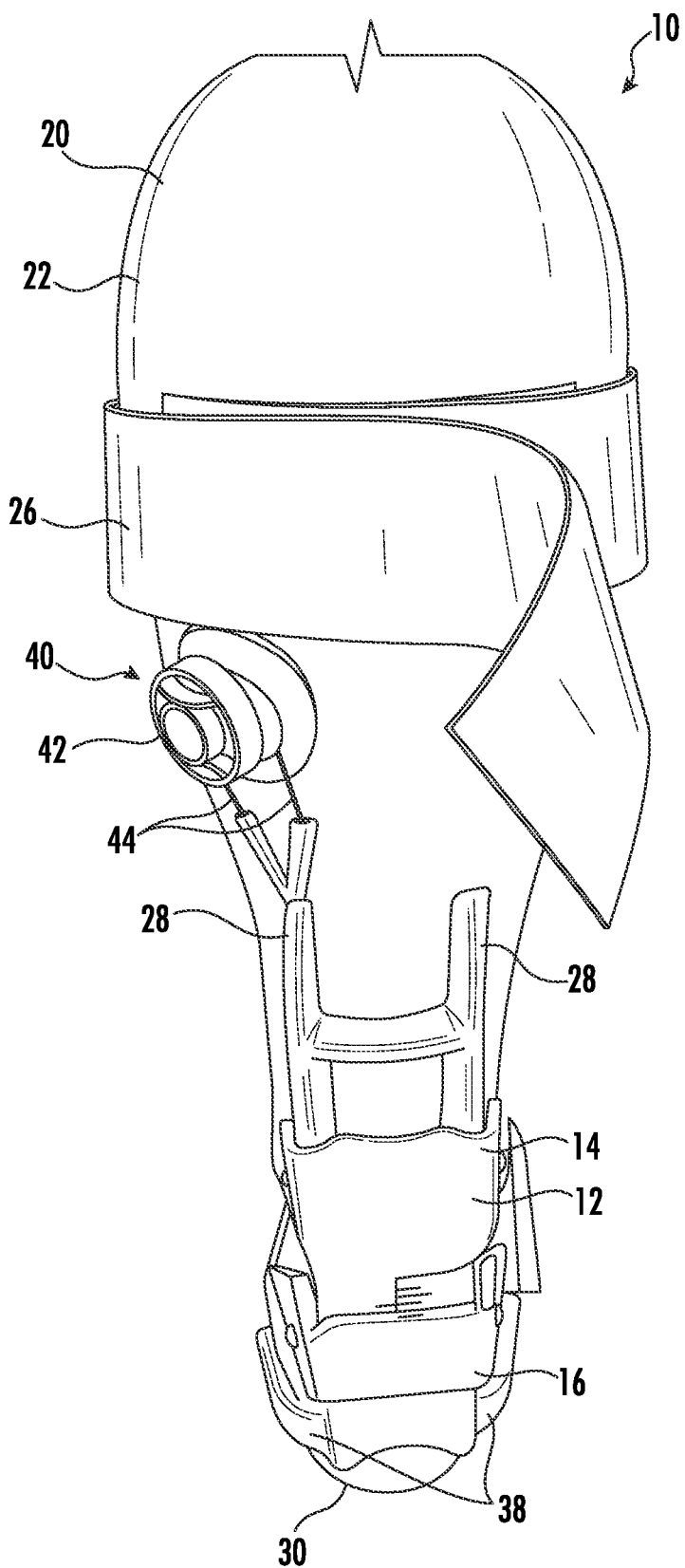
FIG. 2 is a rear view of an embodiment of the lower leg orthotic brace.

For purposes of description herein, the terms "upper," "lower," "right," "left," "rear," "front," "vertical," "horizontal," and derivatives thereof shall relate to the disclosure as oriented in FIG. 2. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
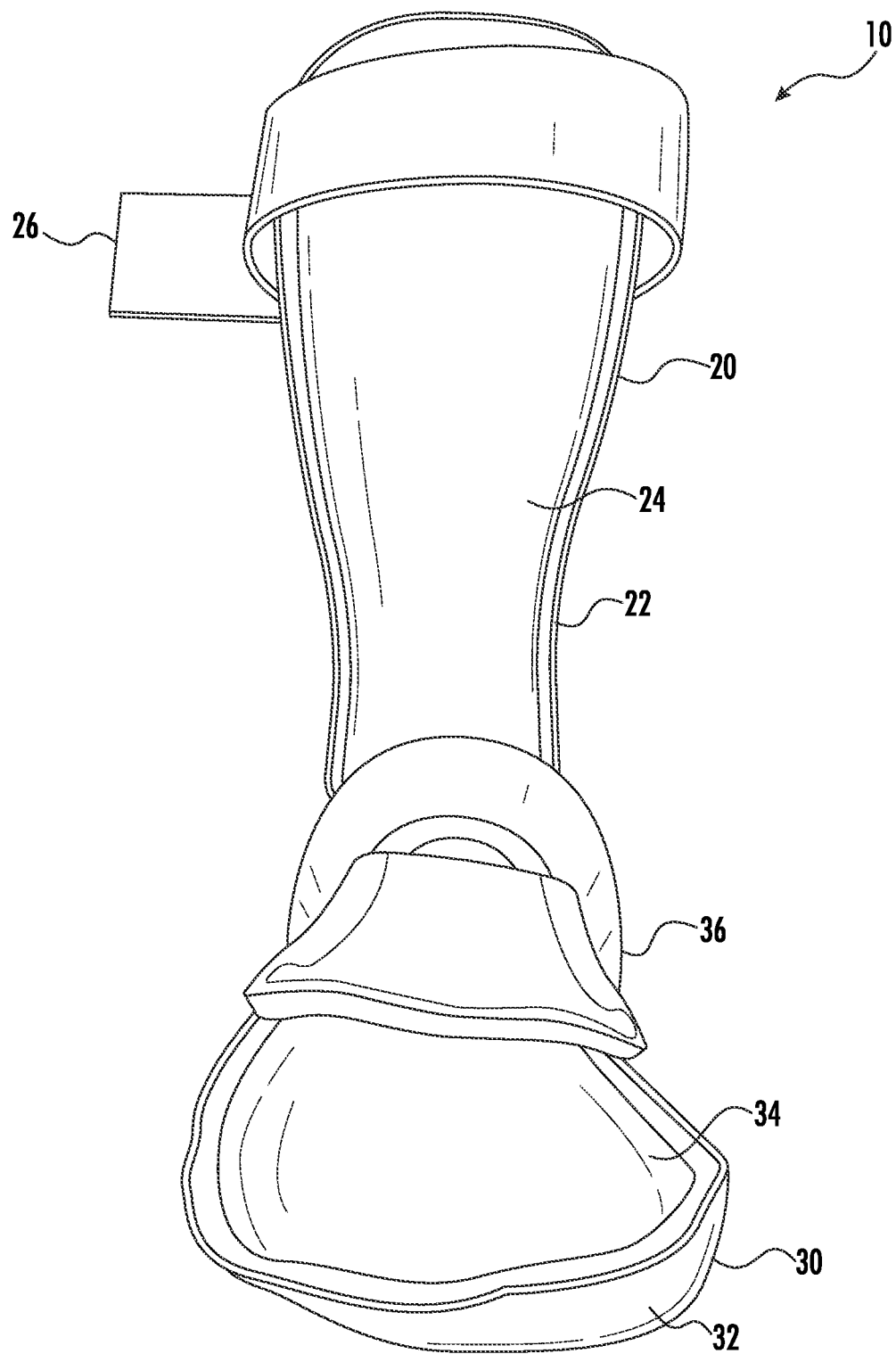
FIG. 1 is a front view of an embodiment of the lower leg orthotic brace.

FIG. 1 shows a foot orthotic or brace 10 for use by a user suffering from an ailment including, but not limited to, inflammation or fibroses tissue such as plantar fasciitis or something similar including inflammatory tendinitis or degenerative tendinosis, pain from bone spurs, and other foot ailments. The brace 10 may be generically formed or may be custom formed to an individual person's lower leg and/or foot. The brace 10 typically provides the support necessary and prevents any movement of the lower leg and foot to allow the ailment to heal intrinsically. Additionally, the brace may be a unitary brace that is a single frame that includes a lower leg support and foot support integral with one another and formed without a hinged connection between a lower leg support 20 and a foot support 30 or, as discussed below, the brace may be hingedly connected to one another.

The brace may include a lower leg support 20 and a foot support 30. The lower leg support 20 and the foot support 30 may be hingedly connected to one another. As shown in the various figures, the lower leg support 20 and the foot support 30 may be connected by a hinge 12. The hinge may be any type/style hinge that facilitates movement of the lower leg support 20 relative to the foot support 30. The hinge shown in the embodiment of FIGS. 6-10 has the ability to move through a larger range of motion than the hinge of the embodiment shown in FIGS. 1-4. The range of angle/orientation may be adjusted based upon the location of the lower leg support and the foot support when the screw 13 is tightened. The range may be positioned from anywhere from 20 degrees flexion to about 40 or even about 45 degrees extension typically at five or ten degree intervals for adjustment. As shown in FIGS. 6-10, the intervals are 10 degree intervals.

Figure 3:
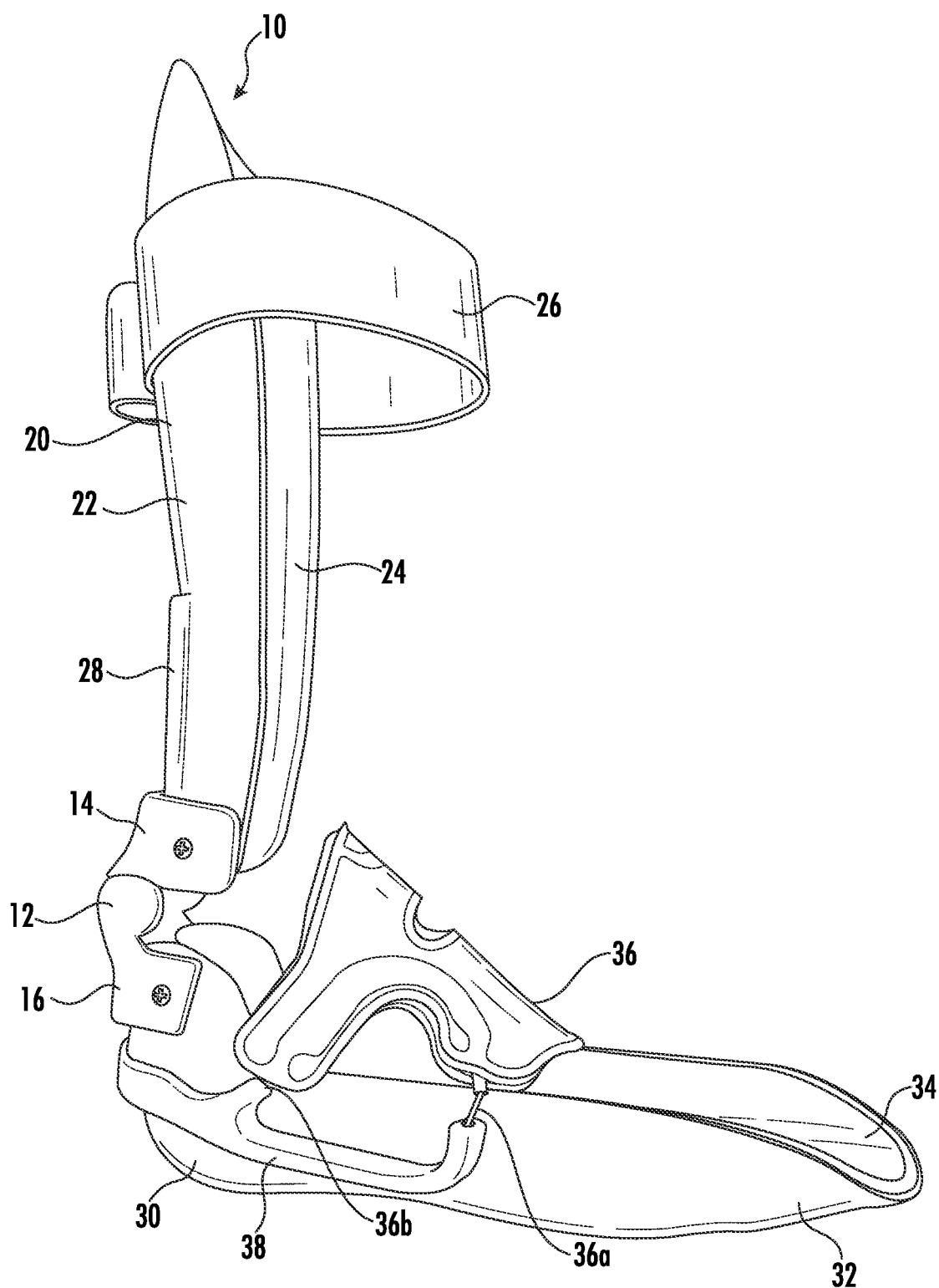
FIG. 3 is a side view of an embodiment of the lower leg orthotic brace.

The lower leg portion supports at least a portion or all of the rear calf of a person's leg and typically extends downward to the hinge 12 positioned proximate the pivot point of plantarflexion and dorsiflexion of the foot. The hinge 12 may include an upper portion 14 fixedly attached to or integrated into the lower leg support 20 at a lower end of the lower leg support 20, and a lower portion 16 of the hinge 12 fixedly attached to or integrated into a rear end of the foot support 30. The hinge upper portion 14 and lower portion 16 are rotatably attached to one another. This rotatable attachment may be in any manner known in the art such as a pin that is disposed between the upper and lower portions 14, 16, a living hinge design, or may be a cylindrical press fit that allows for rotational movement between the two parts 14, 16 as shown in FIGS. 2 and 3. The hinge is designed and located specifically to locate the user's leg and foot in a neutral position to allow for soft tissue rehabilitation.

The lower leg support 20 may include an outer shell 22, an inner liner 24, and an adjustable strap 26 that attaches to itself, typically using a hook and loop fastening option. The hooks of the hook and loop fastening system are typically on the entirety of the interior facing portion of the strap 26 and the loops of the system are typically on the entirety of the exterior facing portion of the strap 26. However, the hook and loops may be reversed and only present on a portion of the strap as well.

Figure 4:
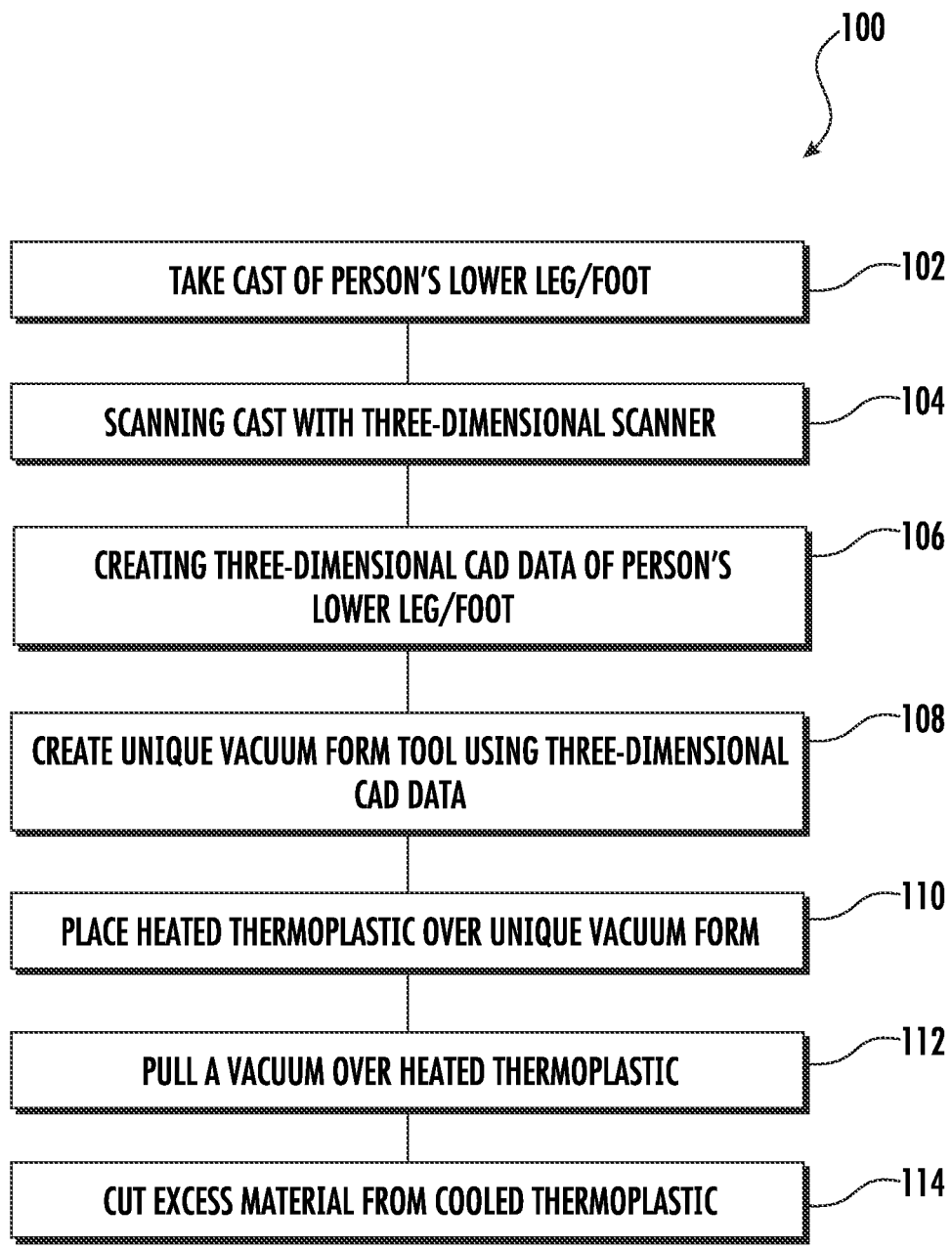
FIG. 4 is a process chart showing the steps for producing an embodiment of a lower leg orthotic brace.

The outer shell 22 may be a custom fit to the patient's own lower leg using a process 100 as shown in FIG. 4 or more typically a semi-custom fit lower leg portion by taking measurement of the wearer's calf at the mid-calf and superior ankle locations of the wearer's leg and extrapolating the measurement/fit of the lower leg portion using those two measurements. Obviously, additional measurements along the length of the lower leg will create an even greater custom fit, but it has been found that the use of the above two measurements is sufficient in nearly all cases to provide a lower leg outer shell 22 that is comfortable for frequent wear. If a completely custom molded outer shell 22 is desired, a cast may be attempted of the user's leg as shown at 102, and using the cast or a 3D imaging scanner used to make a detailed and accurate image/impression/dimensional picture of the user's leg and scanning the cast as shown at 104 using a three-dimensional scanner to create a computer aided design (CAD) model of the leg at step 106. The CAD of the leg is then used in step 108 to create a unique and custom tool on, for example, a Computer Numerical Control (CNC) machine. The tool is then placed in a vacuum form machine at step 110 and a thermoplastic sheet is placed over the custom tool. Then at step 112 a vacuum is pulled over the heated thermoplastic to match the custom form in the tool. Any excess material is then cut away at step 114, leaving the custom formed lower leg outer shell 22.

The inner liner 24 is then fit into the outer shell 22. The inner liner 24 may be a material that is comfortable for the user in that it off loads pressure points of the foot and ankle. The material may be Plastazote® or any other closed cell foam material. A strap 26 may be attached to the lower leg support 20 to securely hold the user's leg in the lower leg support 20. The strap may be adjustable, and may be securely fastened to the lower leg support 20 on one end by sewing or any other secure fastening device known in the art. The strap 26 may include on the opposite end a hook and loop fastener, a buckle, or any other attachment mechanism known in the art that allows the user to pull the strap tightly around the user's leg at the user's preference, but tight enough to hold the leg in the desired position within the brace 10. Preferably, an attachment mechanism that may be engaged and disengaged using either one hand or two is used. In some instances, the ability to engage and disengage this attachment system using only one hand is beneficial.

The foot support 30 may include an outer shell 32, an inner liner 34, and an adjustable tongue 36. The tongue is uniquely comfortable and useable for the particular purpose of the present disclosure. The tongue is typically a pressure dispersing tongue that distributes pressure across the top of the foot. The material is typically a urethane foam with a stretchable nylon backing. The material typically has a silver thread to antibacterial properties. A material that may be used is MP SPONGE+X-STATIC™ from Mat Plus, Inc. in ZPainesville, Ohio. The material is an open cell cellular sponge rubber that allows for air and perspiration transfer through the material over time. The material in conjunction with the pattern of border threading/stitching on the lateral sides, as seen in at least FIG. 3, which establishes a tunnel for the tightening cables 44 to follow within the tongue in a generally archuous pathway along the sides of the tongue to prevent the tightening cables from providing downward force directly across the top of the foot and thereby providing only indirect force, by application of the softer material of the tongue only to the top portion of the foot. This is particularly advantageous given the dense neurovascular bundle that travels over the dorsal portion of the human foot. This prevents significant pain to the wearer that would otherwise often occur if the tightening cables extended over the top of the foot. For this reason, the preferred embodiments of the present disclosure do not typically utilize the tightening cables of the present brace in a manner such that they or the force applied by them extend directly over the top of the foot. In fact, there is typically not any strap or other direct force application such as via a hook and loop strap over the top portion of the foot. The comfort and ease of use is also achieved by the shape of the tongue. While the tongue may be any shape that covers the top of the wearer's foot, the shape of the tongue in a generally hourglass (See FIG. 5). Additionally, the tongue, as shown in the figures, may be connected to the remainder of the orthotic device, typically the foot support 30 by only the tightening cables and/or other portions of the cinching mechanism.

The configuration and use of the tightening cables optionally along with the cinching mechanism 40 when the tightening cables are positioned within the arch-shaped side channels of the tongue, according to the present disclosure, may also be used in a variety of other footwear and sporting equipment. In particular, this configuration may be utilized in ski boots, in-line skates, work boots with steel toes, waterproof footwear, kids' shoes, and adult shoes, snow shoes, basketball shoes, and any other footwear where ankle or foot support is beneficial for the use of the footwear. In particular, one cinching mechanism or a plurality cinching mechanisms may be used with one or more straps or tongues, typically padded tongues are particularly useful in footwear or orthotic braces where the insertion of the foot is typically difficult or tight when the cinching mechanism(s) are not employed. A variety of cinching mechanisms can be employed. For example, LOCK LACES® available at www.locklaces.com and from Positive Distribution LLC of 4608 Industry Ln, Ste. H Durham, NC may be employed. Another example of a cinching mechanism that could be employed in connection with a brace of the present disclosure may be a speed zone lace kit from SKI PRO® which has a cross finger grip and bungie string that can be tied off and/or held in position with one or more clasps. In the case of molded footwear and sporting goods, such as in-line skates and ski boots, for example, the tightening cable channels of the present disclosure within the lower leg support may be similarly employed in connection with these other footwear devices. The rotatable knob 42 of the present disclosure is typically placed high on the orthotic brace, but could be placed on the side of the foot in other footwear or up higher on the footwear in the case of the in-line skate and ski boot or waterproof footwear where there is a portion of the footwear that extends up from the ankle along the calf. Typically, the knob 42 is placed as high as functionally possible to allow it to be as easily accessed, but the knob 42 may be located at any location of the footwear or brace. It is also possible to use a second or additional cinching mechanism along with a broad anterior leg retainer/strap that can be cinched down quickly and easily if such a strap is desired for the orthotic brace or footwear device. Instead of a rotatable knob, a push button and cable cinching mechanism may be employed.

Figure 5:
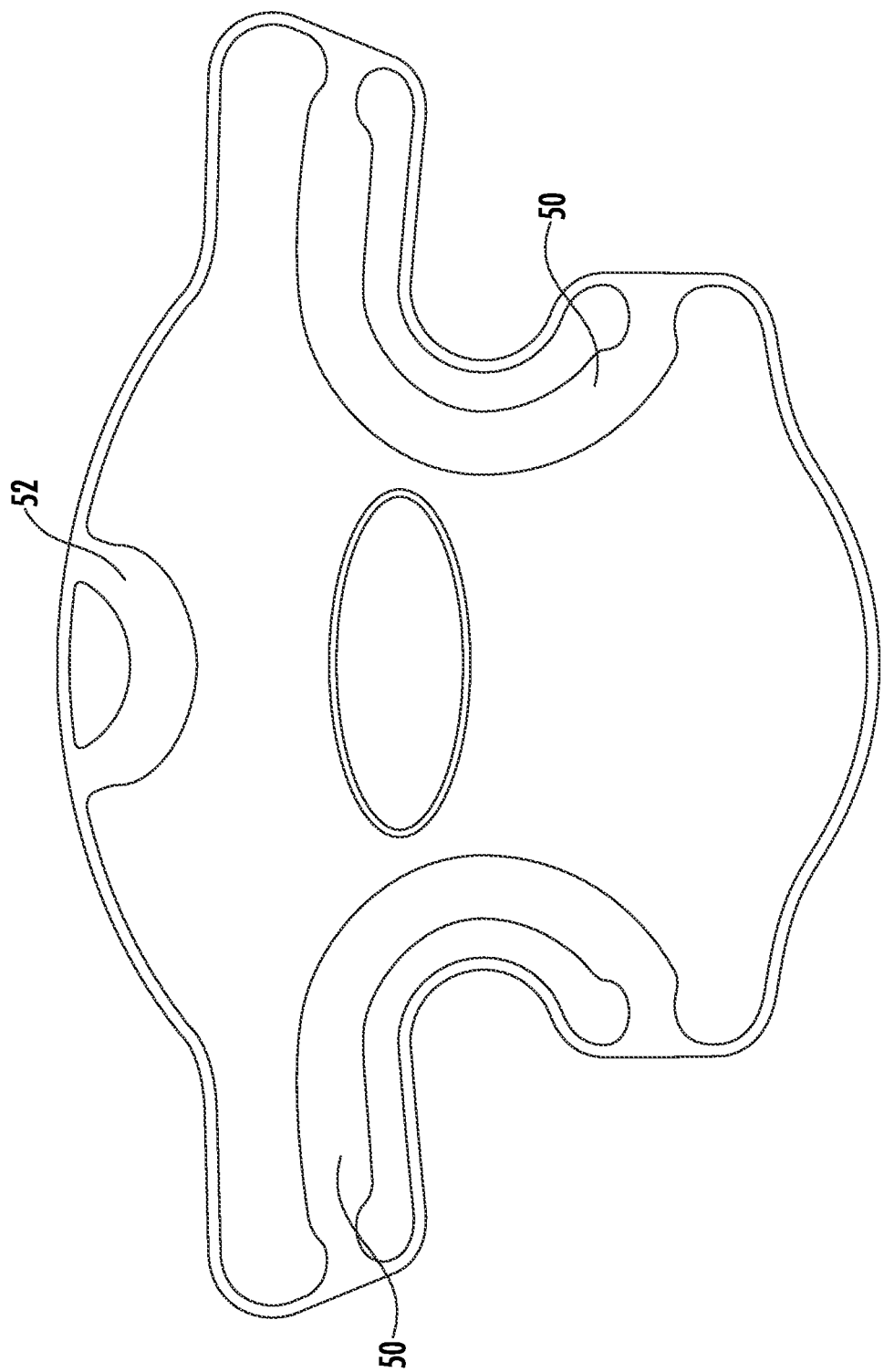
FIG. 5 is a top view of a tongue design with left and right side tightening cable mechanism retaining channels and a top elastic tongue elevating handle receiving channel.
Figure 6:
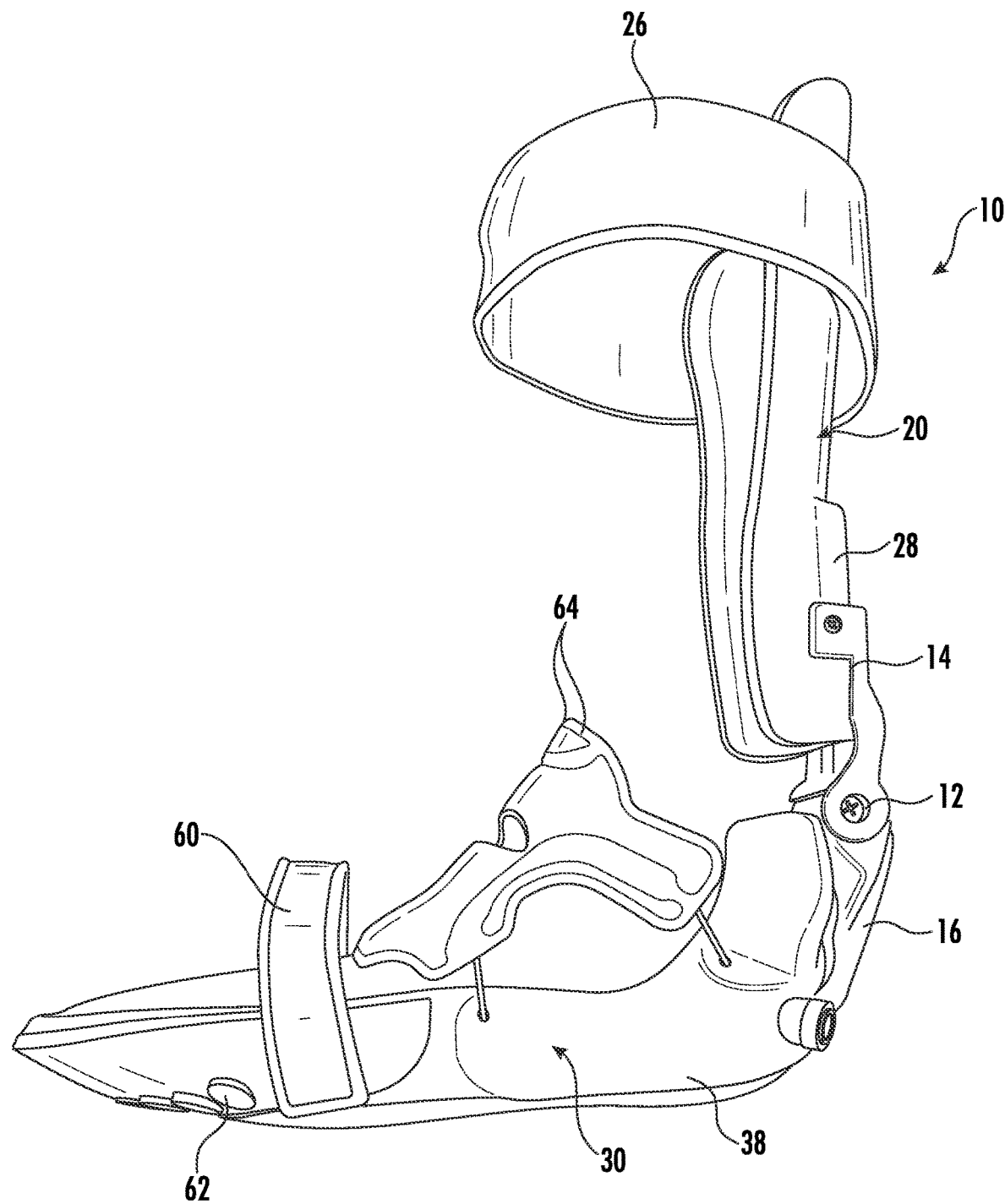
FIG. 6 is an elevated side view of another embodiment of the lower leg orthotic brace.
Figure 7:
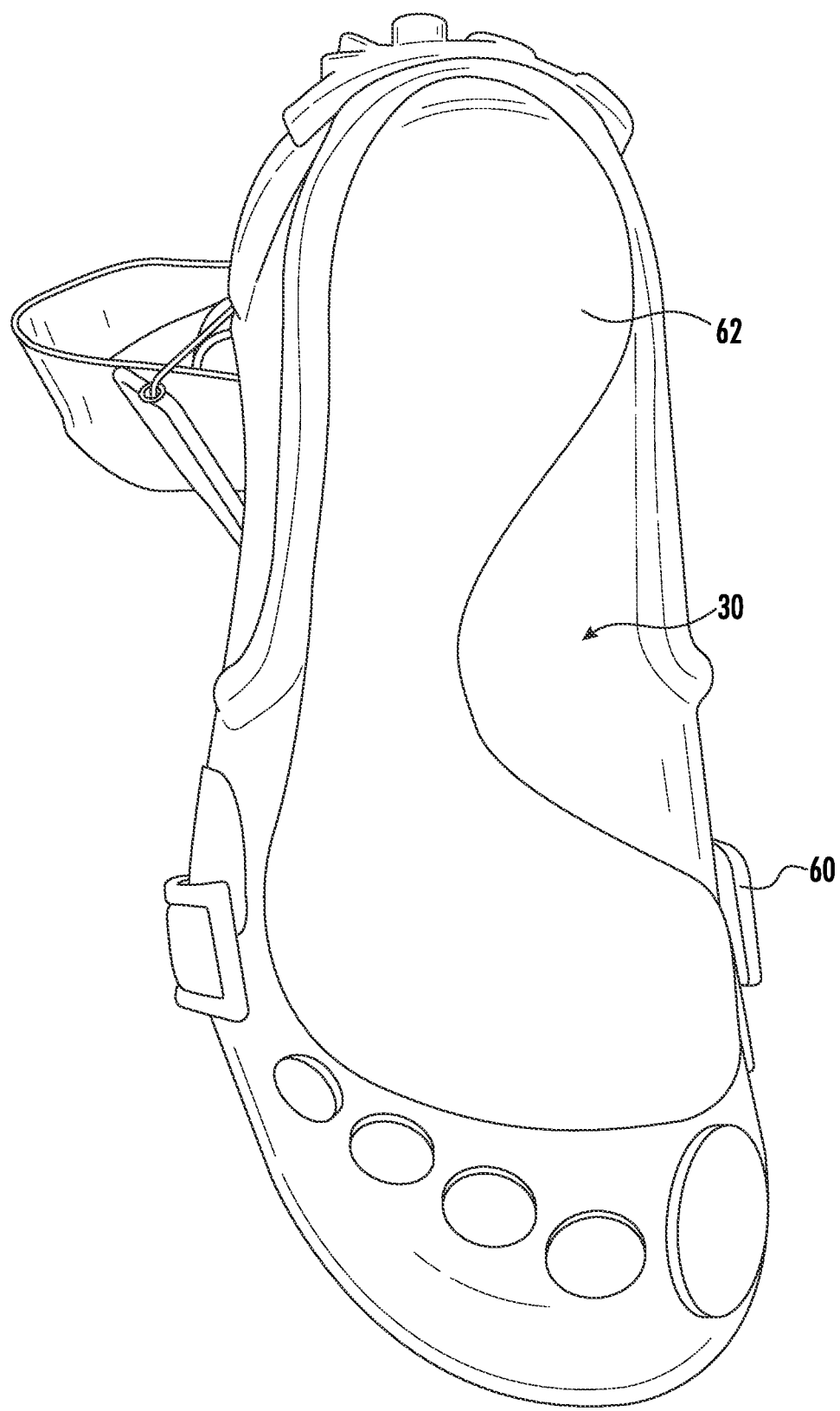
FIG. 7 is a bottom view of the lower leg orthotic brace shown in FIG. 6.
Figure 8:
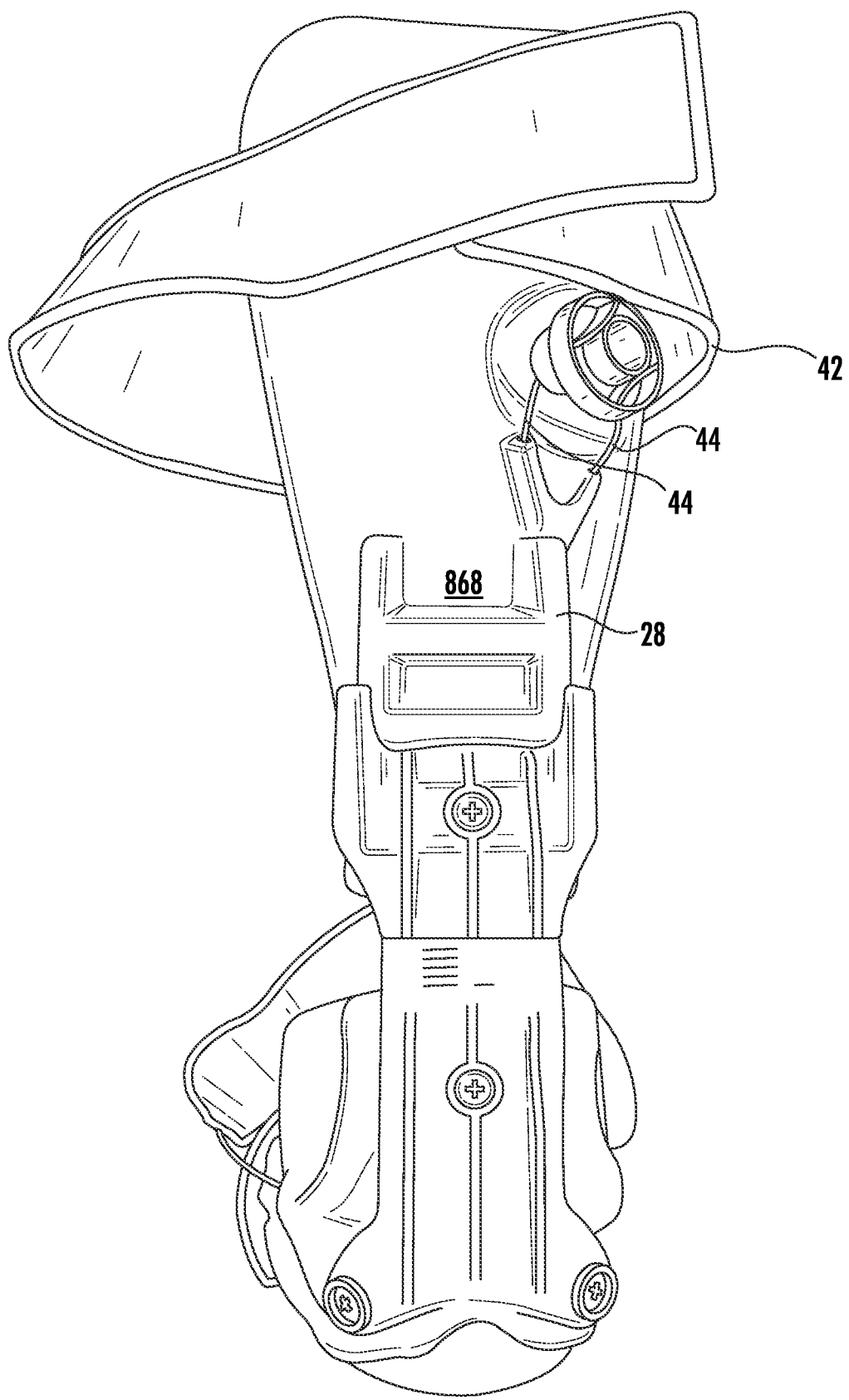
FIG. 8 is an elevated rear view of the lower leg orthotic brace shown in FIG. 6.
Figure 9:
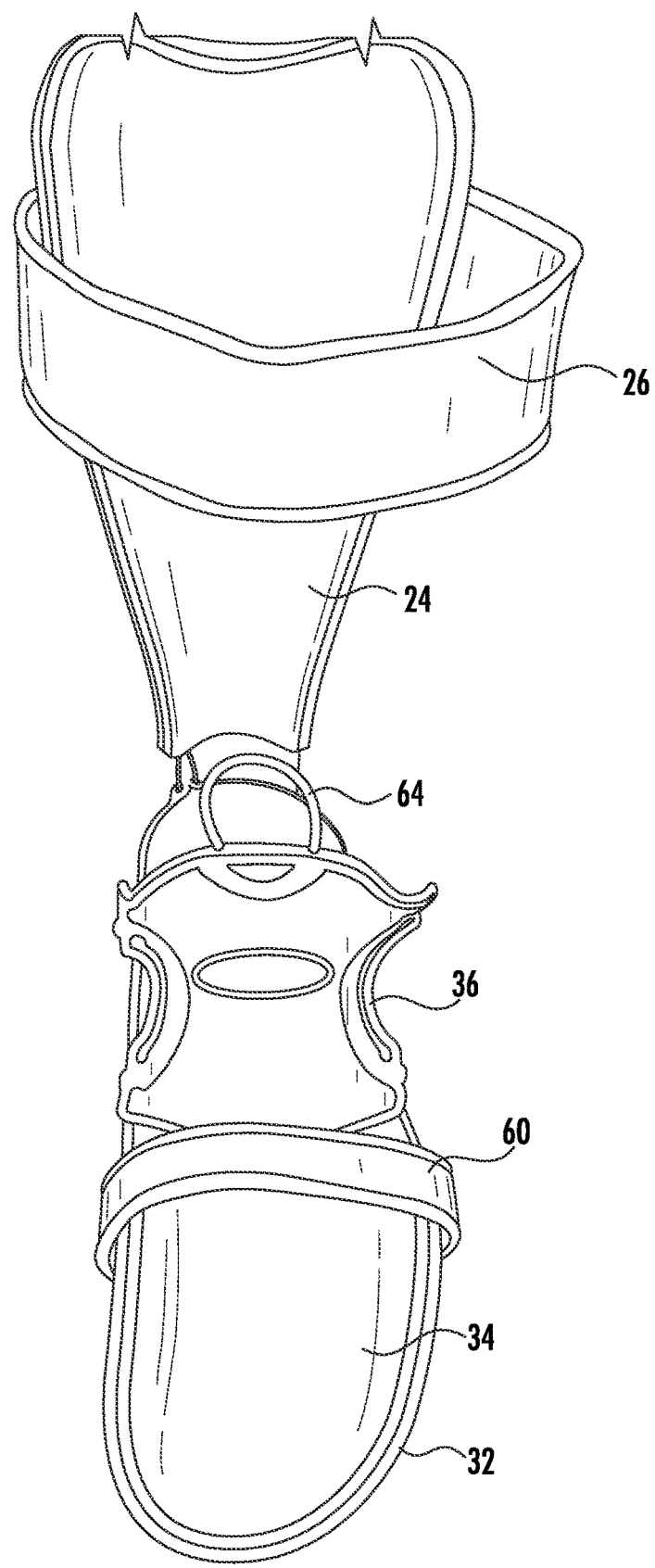
FIG. 9 is a front perspective view of the lower leg orthotic brace shown in FIG. 6.
Figure 10:
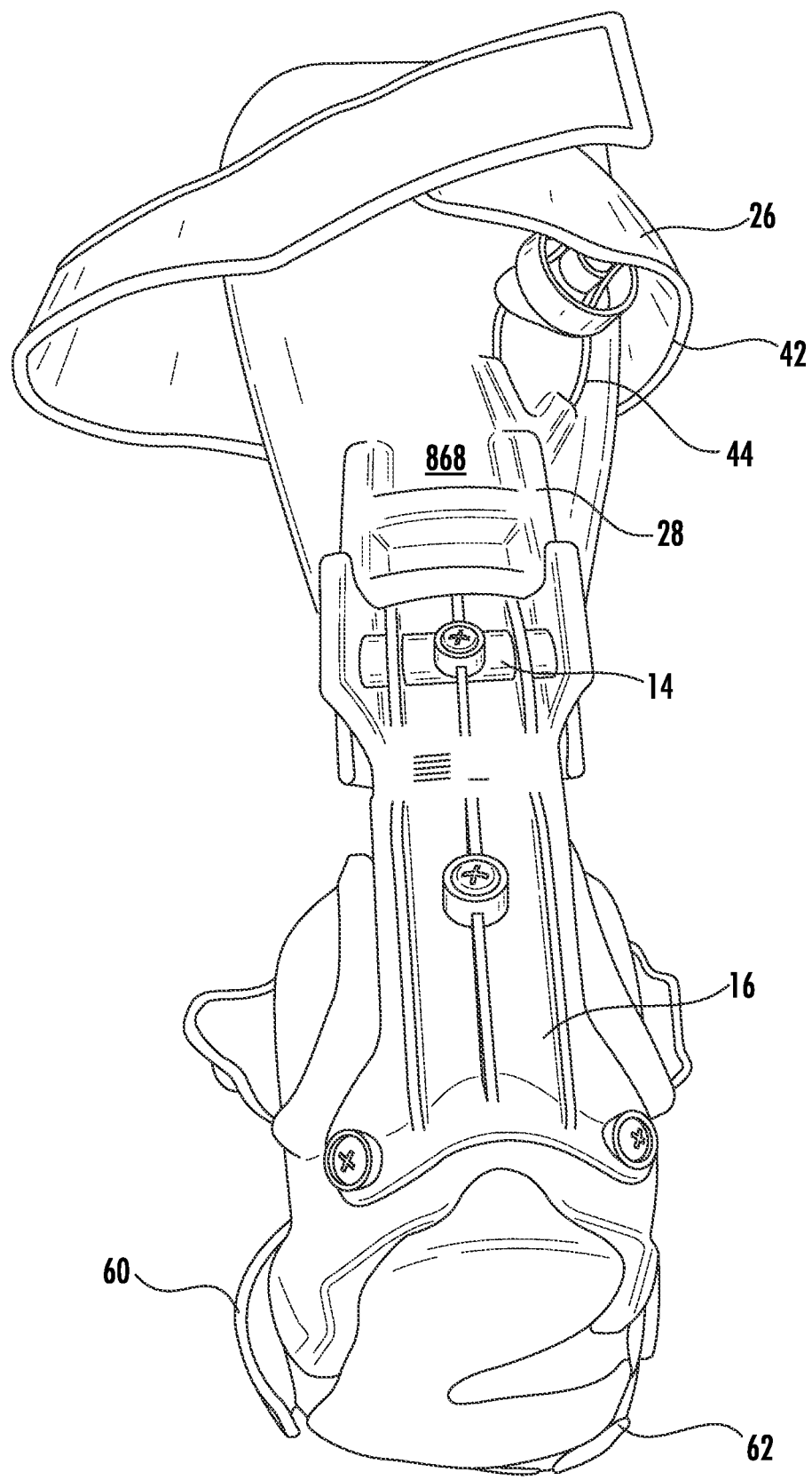
FIG. 10 is a bottom rear perspective view of the orthotic brace shown in FIG. 6.

An alternative tongue is shown in FIG. 5. The tongue shown in FIGS. 5-10 has two tightening cable receiving channels 50 and a top channel 52. The top channel typically receives a flexible, stretchable cable that forms a loop that may be grasped by a user during use in the area between the flexible, stretchable cable and the material of the tongue in the space as shown in FIG. 9, for example. This elastic loop 64 (See FIG. 9) allows the user to easily grasp and loosen or move the tongue into the appropriate position prior to tightening the tightening cables with the tightening mechanism.

The outer shell 32 may be a universal brace that is not custom fit to a particular patient or may be a custom fit to the patient's own foot. This is done by taking a foam impression of the user's foot, and the foam impression of the user's foot is used to create a computer aided design (CAD) model of the foot by scanning the foam impression with a 3D scanning machine. The CAD of the foot is then used to create a unique and custom tool on, for example, a CNC machine. The tool is then placed in a vacuum form machine and a thermoplastic sheet is placed over the custom tool. A vacuum is then pulled over the heated thermoplastic to match the custom form in the tool. Any excess material is then cut away, leaving the custom formed foot outer shell 32. Instead of or in addition to the use of a foam impression, a three dimensional scanned image of the wearer's foot alone may be used to create the computer aided design model of the foot. Any system that can take an accurate impression of the individual's foot dimensions may be used. The foam impression allows for the systems and custom braces to be used in more remote areas where 3D scanning systems may not be available. The foam impression is helpful to show the weight bearing position of the wearer and is most typically used for this reason.

The inner liner 34 is then fit into the outer shell 32. The inner liner 34 may be a material that is comfortable for the user in that it off loads pressure points of the foot and ankle. The material may be Plastazote® (a closed cell cross-linked polyethylene foam) or any other closed cell foam material. The tongue 36, which was discussed in greater detail above, may be attached to the foot support 30 to hold the user's foot securely in the foot support 30. The tongue 36 may be adjustable, and may include a hook and loop fastener, a buckle, or any other attachment mechanism known in the art.

In an embodiment, the tongue may be tightened from a release position to a secure position and loosened from the secure position to the release position with a cinching mechanism 40. The cinching mechanism may include a rotatable knob 42 and one or more tightening cables 44. The tightening cable may be attached to the knob 42 such that when the knob 42 is rotated, the available slack within the tightening cable 44 is reduced and tension increased on the tightening cable 44. The knob 42 is typically easily rotatable using one hand when the orthotic brace is in use.

The lower leg support 20 and the foot support 30 may include one or more channels 28, 38, that the tightening cable 44 is routed through. The channels may run along the back side of the lower leg support outer shell 22 and the bottom side of the foot support outer shell 32, although the channels may be located in any convenient location. The channels may be integrally formed within the outer shells 22, 32, that are not capable of being removed by hand and without the use of tools or may be separate parts that are added to the outer shells later in assembly. The particular shape or pattern of the channels are not critical, but the channels should allow the cable within to easily move within the channels. The cable 44 may also run through cavities within the hinge 12, completely shielding and protecting the cable 44 from the external environment and thus external damage. The cable 44 may be attached to the tongue 36 at forward and rearward points 36a, 36b, while the opposite side of the tongue is securely fastened to the lower leg support 30. When the knob 42 is rotated, slack in the cable 44 is taken up within the knob and tension is applied to the cable 44. This tension pulls the tongue tight across the user's foot, while the channels 28, 38 protect the cables from snagging.

The cinching mechanism 40 provides a fast and easy way for a user to insert the user's foot into the brace with an extra wide entry aperture under the tongue (the tongue is loose) while still allowing for rapid securing of the tongue onto the surface of the foot to secure the foot quickly and comfortably within the brace. The breadth of the wide entry aperture may be adjusted by the user. This is a significant improvement that allows all users, but particularly users with limited mobility or elderly users to more easily insert their foot and leg into the brace and quickly retain the foot and lower leg within the brace. The cabling provides additional foot entry space by extending the tongue away from the foot support outer shell 32 the added distance provided by the cabling. The tongue is typically not directly connected to the lower leg support or the foot support other than via the cable.

A sensor or sensors may also be positioned within the cavity of the brace or footwear to measure pressure or temperature within the cavity. The sensor or sensors employed are typically used to ensure compliance with the wearing of the brace when employed in connection with an orthotic brace. The sensor will typically also include a wireless communication system/module that will communicate via BLUETOOTH™, cellular, Wi-Fi or other wireless communication system or systems such that the brace determines compliance with the wearing of the brace for the time period each day proscribed by a caregiver. Alternatively, the sensor may sense the presence or absence of a foot within the brace, store the sensed information and thereafter communicate once or periodically during a day or when the device is connected with a computing device via a wired connection. In such a case, the wireless communication ability of the orthotic brace or footwear would not be necessary, but could be included. A mobile application on a portable computing device incorporating memory and a processor may be used to display data to the wearer or the caregiver regarding compliance. Data displayed may include the time each day the device is worn, for example. The sensor or sensors employed may be pressure sensors or a temperature sensor, which typically uses a thermistor(s). If a pressure sensor is used, the sensor is typically positioned within the foot support instead of the lower leg support so that weight from the wearer will more readily be felt by the sensor and more consistent data on use compliance may be obtained, but conceivably the pressure sensors could be positioned on the lower leg support as well or instead so long as they are sensitive enough to sense the pressure from the back of the person's leg. In addition, a light sensor might also be employed, but this may be too easy for the wearer to circumvent if the wearer simply blocked the light sensor location with something like tape. However, a light sensor or a combination of a light, pressure and/or temperature sensor may be employed in one or a plurality of locations on or within the orthotic brace. Conceivably, the sensor may be molded into the upper portion or the lower portion.

Regarding the embodiment shown in FIGS. 6-10, it is noteworthy that this embodiment utilizes a separate foot restraining strap 60 engaged to the orthotic brace using a hook and loop fastening system. A portion of the hook and loop fastener is attached to each side of the foot support and to the engagement side of the foot support. The fastener attaches to the hook or loop fastener portion that is located on the side of the foot support. A slip resistant surface material 62, which is shown as the shape of a foot in the embodiment of the figures but could be any shape, may be employed on the bottom of the orthotic brace. Typically, more of the bottom surface of the brace will be covered than not in order to better prevent the brace from slipping during use.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

The invention claimed is:

1. A custom foot orthotic comprising:
    a foot support that is custom fit to a user's foot, the foot support comprising:
        a thermoplastic outer shell;
        a closed cell foam liner within the thermoplastic outer shell; and
        a tongue having a leg facing edge, a bottom edge, a lateral side edge and a medial side edge and wherein the tongue has a lateral side receiving channel proximate the lateral side edge of the tongue and wherein the lateral side receiving channel extends from a lateral side proximal end opening proximate the leg facing edge of the tongue to a lateral side distal end opening distal from the lateral side proximal end opening and a medial side receiving channel proximate the medial side edge of the tongue and wherein the medial side receiving channel extends from a medial side proximal end opening proximate the leg facing edge of the tongue to a medial side distal end opening distal from the medial side proximal end opening;
    a lower leg support that is custom fit to a user's lower leg, the lower leg support comprising;
        a thermoplastic outer shell;
        a closed cell foam liner within the thermoplastic outer shell; and
        a strap to secure the user's leg within the lower leg support;
    a cinching mechanism comprising:
        a rotatable tightening knob disposed on the lower leg support; and
        a tightening cable coupled to the rotatable tightening knob; and
    a plurality of channels within the lower leg support and a plurality of channels within the foot support; and
    wherein the tightening cable is routed through the plurality of channels within the lower leg support, the plurality of channels in the foot support, the lateral side receiving channel and the medial side receiving channel and the tightening cable of the cinching mechanism shortens and elongates in response to movement of the rotatable tightening knob and wherein the tightening cable is not configured to pass over a bridge of the user's foot.

2. The custom foot orthotic of claim 1, wherein the lateral side receiving channel is an archuous pathway along the lateral side edge of the tongue and wherein the medial side receiving channel is an archuous pathway along the medial side edge of the tongue.

3. The custom foot orthotic of claim 2 further comprising a lockable hinge disposed between the foot support and the lower leg support and wherein the tongue further comprises an aperture within the tongue wherein the aperture is configured to be positioned proximate a center of the tongue and over a dorsal portion of the user's foot when in use.

4. The custom foot orthotic of claim 3, wherein the lockable hinge includes markings for a user to lock the lockable hinge in any angle and are positionable between a 20 degree flexion angle and a 40 degree extension angle between the foot support and the lower leg support in 10 degree increments.

5. The custom foot orthotic of claim 4, wherein the tightening cable is adapted to tighten and loosen the tongue in response to rotating the rotatable tightening knob and wherein the aperture within the tongue is positioned over a bridge of a foot when the foot is within the foot support and the tongue is in an engaged position over the top of the foot of a wearer.

6. The custom foot orthotic of claim 1, wherein the tightening cable is wound around the rotatable tightening knob and wherein the leg facing edge extends between the lateral side and the medial side and wherein the tongue further comprises a loop engaging channel extending between and interconnecting a first loop engaging channel opening on the leg facing edge of the tongue and a second loop engaging channel opening on the leg facing edge of the tongue and a loop of a flexible cable positioned within the loop engaging channel such that a portion of the loop is within the loop engaging channel and a portion of the loop extends beyond the leg facing edge of the tongue and out of the first loop engaging channel opening and out of the second loop engaging channel opening.

7. The custom foot orthotic of claim 6, wherein the rotatable tightening knob is rotated to tighten the custom foot orthotic to the user's foot and wherein the lateral side receiving channel is an archuous pathway along the lateral side of the tongue and wherein the medial side receiving channel is an archuous pathway along the medial side of the tongue.

8. The custom foot orthotic of claim 7, wherein the tongue further comprises an upper surface and a lower surface, and an aperture configured to be positioned at a center of the tongue and over a dorsal portion of the user's foot wherein the aperture is an unobstructed opening extending between the upper surface to the lower surface and wherein the flexible cable is a flexible and extendable cable.

9. The custom foot orthotic of claim 1, wherein the tongue further comprises an ankle facing channel having a loop of material disposed there and extending outside the ankle facing channel to form a handle and wherein the lower leg support is hingedly connected to the foot support.

10. The custom foot orthotic of claim 1, wherein the foot support and the lower leg support form a unitary structure and wherein the plurality of channels in the lower leg support are integrally formed within the thermoplastic outer shell of the lower leg support and not capable of being removed by hand and without the use of tools and the plurality of channels in the foot support are integrally formed within the thermoplastic outer shell of the foot support and not capable of being removed by hand and without the use of tools.

11. A brace for a person's lower leg and foot comprising:
a foot support having a thermoplastic outer shell with a foot support cable receiving channel and a foam liner within the thermoplastic outer shell;
a lower leg support hingedly connected to the foot support, the lower leg support having a thermoplastic outer shell with a lower leg cable receiving channel, a foam liner within the thermoplastic outer shell, and a strap engaged to the thermoplastic outer shell on a first end and a hook and loop fastening system on a second end such that the strap wraps around a wearer's lower leg and secured using the hook and loop fastening system of the strap;
a tongue having a lateral side edge and a medial side edge and wherein the tongue has a lateral side receiving channel extending from a lateral side proximate end to a lateral side distal end and proximate the lateral side edge of the tongue and a medial side receiving channel extending from a medial side proximate end to a medial side distal end and proximate the medial side edge of the tongue;
a rotatable tightening knob disposed on a top portion of the lower leg support; and
a cable coupled to the rotatable tightening knob, the cable routed within the foot support cable receiving channel the lower leg cable receiving channel, the lateral side receiving channel, and the medial side receiving channel, and operably attached to a second end of the tongue to tighten and loosen the tongue into engagement with a bridge of a wearer's foot without applying downward pressure over the bridge of the wearer's foot from directly over the bridge of the wearer's foot and wherein the cable is not configured to pass over a bridge of the wearer's foot.

12. The brace of claim 11 further comprising a lockable hinge disposed between the foot support and the lower leg support and wherein the lockable hinge includes markings for a user to lock the lockable hinge in positions at 10 degree intervals.

13. The brace of claim 12, wherein the tongue further comprises an aperture positioned over the bridge of the wearer's foot when the tongue is in an engaged position with the wearer's foot.

14. The brace of claim 13, wherein the foot support cable receiving channel comprises a plurality of foot support cable receiving channels integrally formed within the thermoplastic outer shell of the foot support and the lower leg support comprises a plurality of lower leg cable receiving channels integrally formed within the thermoplastic outer shell of the lower leg support.

15. The brace of claim 11, wherein the foot support is custom fit to a wearer's specific foot and the lower leg support is custom fit to at least a portion of the wearer's lower leg and wherein the tongue comprises an aperture proximate a center of the tongue.

16. The brace of claim 11, wherein the cable is adapted to tighten and loosen the tongue in response to rotating the rotatable tightening knob.

17. The brace of claim 11, wherein the rotatable tightening knob is rotated to tighten the brace to a user's foot and wherein the lower leg support and the foot support may be adjusted at 10 degree intervals between the 20 degree flexion position and the 40 degree extension position.

18. The brace of claim 11, wherein the rotatable tightening knob is pushed or pulled to release tension on the cable and further comprising a pressure sensor or a temperature sensor or both a pressure sensor and a temperature sensor within the brace and wherein the tongue is not directly connected to the lower leg support or the foot support other than via the cable.

19. The brace of claim 11, wherein the tongue further comprises an upper surface and a lower surface, and an aperture configured to be positioned at a center of the tongue and over a dorsal portion of the foot wherein the aperture is an unobstructed opening extending between the upper surface to the lower surface.

20. A brace for a person's lower leg and foot comprising:
a foot support that is fit to a user's foot, the foot support comprising:
a thermoplastic outer shell;
a closed cell foam liner within the thermoplastic outer shell; and
a tongue to secure the user's foot within the foot support comprising a lateral side edge and a medial side edge; a lateral side receiving channel extending from a lateral side proximate end to a lateral side distal end and proximate the lateral side edge of the tongue; and a medial side receiving channel extending from a medial side proximate end to a medial side distal end and proximate the medial side edge of the tongue;
a lower leg support connected to the foot support, the lower leg support comprising;
a thermoplastic outer shell; and
a closed cell foam liner within the thermoplastic outer shell;
a cinching mechanism comprising:
a rotatable tightening knob disposed on an upper end of the lower leg support; and
a tightening cable coupled to the rotatable tightening knob and operably connected to the foot support; and
a plurality of tightening cable receiving channels within the lower leg support and the foot support; and
wherein the tightening cable is routed through the plurality of tightening cable receiving channels within the lower leg support and the foot support and through the lateral side receiving channel and the medial side receiving channel.

* * * * *